(12) United States Patent
Cattani

(10) Patent No.: US 6,817,842 B2
(45) Date of Patent: Nov. 16, 2004

(54) DEVICE FOR REGULATING COMPRESSORS OR ASPIRATORS

(75) Inventor: Ennio Cattani, Parma (IT)

(73) Assignee: ESAM S.p.A., Parma (IT)

( * ) Notice: Subject to any disclaimer, the term of this patent is extended or adjusted under 35 U.S.C. 154(b) by 30 days.

(21) Appl. No.: 10/156,828

(22) Filed: May 30, 2002

(65) Prior Publication Data
US 2003/0044295 A1 Mar. 6, 2003

(30) Foreign Application Priority Data
Aug. 31, 2001 (IT) .................................. MO2001A0176

(51) Int. Cl.[7] .............................................. F04B 49/00
(52) U.S. Cl. ...................................... 417/278; 137/79
(58) Field of Search ......................... 417/278; 137/78.5, 137/79, 81.1, 540, 543.17

(56) References Cited

U.S. PATENT DOCUMENTS

| | | | | |
|---|---|---|---|---|
| 2,410,522 A | * | 11/1946 | Powell | ......................... 417/278 |
| 3,918,848 A | | 11/1975 | Benson | |
| 4,848,389 A | * | 7/1989 | Pirkle | ........................... 137/80 |
| 5,186,613 A | | 2/1993 | Kotlarek et al. | |
| 5,197,671 A | * | 3/1993 | Wass et al. | .................... 137/72 |
| 5,248,244 A | | 9/1993 | Ho et al. | |
| 5,290,154 A | | 3/1994 | Kotlarek et al. | |
| 5,427,132 A | * | 6/1995 | Fenner, Jr. | .................... 137/79 |
| 5,511,576 A | * | 4/1996 | Borland | ........................ 137/79 |
| 5,879,594 A | * | 3/1999 | Holtzman | ..................... 137/79 |
| 6,210,120 B1 | | 4/2001 | Hugenroth et al. | |
| 6,530,391 B1 | * | 3/2003 | Dulin | ........................... 137/79 |
| 6,592,105 B1 | * | 7/2003 | Holtzman | ..................... 137/79 |

FOREIGN PATENT DOCUMENTS

| | | | | |
|---|---|---|---|---|
| EP | 0094457 A1 | * | 11/1983 | ................. 417/278 |
| JP | 57151084 A | * | 9/1982 | ................. 417/278 |

* cited by examiner

*Primary Examiner*—Cheryl J. Tyler
(74) *Attorney, Agent, or Firm*—Browdy and Neimark, P.L.L.C.

(57) ABSTRACT

In a delivery conduit for a compressor or an aspiration conduit for an aspirator, which connects the compressor or the aspirator to a closed environment, a first valve is inserted, and opening and a closing of which is commanded by a temperature of an external environment. The valve is normally closed for external temperatures which are lower than a predetermined level and open, placing the conduit in communication with the outside environment, when the external temperature exceeds the predetermined level.

2 Claims, 1 Drawing Sheet

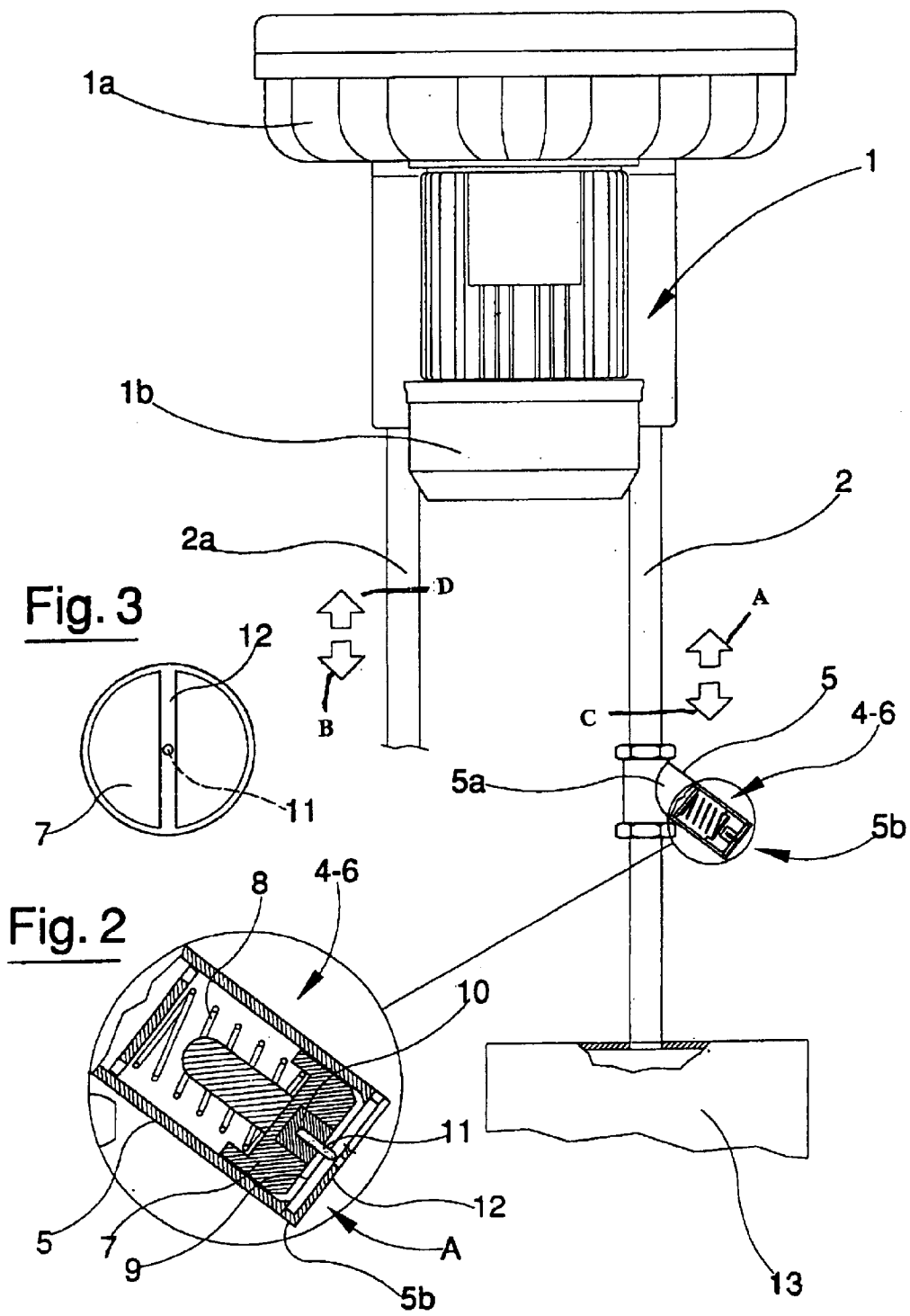

DEVICE FOR REGULATING COMPRESSORS OR ASPIRATORS

BACKGROUND OF THE INVENTION

Specifically, though not exclusively, the invention is usefully applied in dental aspirating apparatus.

In the following description and in the accompanying figures reference is made to an aspirator (a suction or "vacuum" pump) but all of the description could also be applied to compressors.

Aspirators are much-used in dental aspiration plants where a depression has to be created in connection with suction tubes.

It is well-known that the coils of electric motors actuating the aspirators are subject to heating-up: this heating-up increases as the current supply absorbed by the motor increases, which in turn increases in line with the degree of depression required.

To limit this heating-up, a valve is usually provided, usually arranged in the aspiration conduit connecting the aspirator to the environment in which the depression is to be created. When the valve is opened it places the aspiration conduit (or the above-mentioned environment) in connection with the outside. This valve is opened when a predetermined pressure difference is reached between the outside environment and the inside environment, which corresponds to a predetermined electrical current which crosses the motor coils. In this way, without stopping the machine, excessive heating-up is avoided due to over-heating of the motor coils.

The problems encountered with compressors when the internal pressure increases are very similar.

The heat produced by aspirators is dispersed in the outside environment. For this reason the manufacturers always recommend that the machines be located in well-aired and cool places in order for the machine to perform optimally. Unfortunately, for reasons of space, aesthetic preference, or in order to avoid any irritation that might be caused by the admittedly low noise level of aspirators, these machines are often arranged in small and closed places, generally lacking in air; sometimes they are even kept away from the outside environment.

In these conditions, the heat dispersed by the aspirators causes considerable build-up of heat in the surrounding atmosphere, with a consequent heating of the aspirator to beyond realistic limits, causing deterioration in its performance or even faulty functioning and, in particularly grave cases, or in the absence of devices blocking the motor when it reaches dangerous temperatures, a fire hazard. All of the above can happen without the electric current in the coils reaching levels which correspond to a depression level warranting the interjection of the above-cited valve, which would reduce electric current absorption and thus reduce the heat produced by the machine.

If there is a thermal cut-off protection for the motor, a frequent case, the motor is shut down before the aspirator reaches its maximum potential. To prevent machine shutdown, or to reduce its occurrence to an absolute minimum, sometimes the manufacturers themselves calibrate the pressure-differential valves to more prudent levels, thus in effect lowering the potential of the machine and doing an injustice to those users who carefully follow the instructions provided with the machine and locate the aspirator in a correct ambience in order to allow plenty of ventilation.

The main aim of the present invention is to obviate the above-cited drawback in the prior art, by providing a device for regulation of compressors and aspirators which enables the machines to function at maximum potential when the conditions of the outside environment are optimal, but which reduces the machine's performance level when there is an imperfect surrounding environment.

A further aim of the invention is to prevent excessive heating-up of the machine without having to shut the machine down.

An advantage of the device is that it can be applied easily to existing machines. These aims and more besides are all attained by the invention as it is characterized in the claims that follow.

SUMMARY OF THE INVENTION

In a delivery conduit for a compressor or an aspiration conduit for an aspirator, which connects the compressor or the aspirator to a closed environment, a first valve is inserted, and opening and a closing of which is commanded by a temperature of an external environment. The valve is normally closed for external temperatures which are lower than a predetermined level and open, placing the conduit in communication with the outside environment, when the external temperature exceeds the predetermined level.

BRIEF DESCRIPTION OF THE DRAWINGS

Further characteristics and advantages of the present invention will better emerge from the detailed description that follows, of a preferred but nonexclusive embodiment of the invention, illustrated purely by way of example in the appended figures of the drawings, in which:

FIG. 1 is a diagram of either an aspirator or a compressor of the type of the invention;

FIG. 2 is a detail of FIG. 1, in section and in enlarged scale, relating to the valve of the device of the invention;

FIG. 3 is a view in the direction indicated by arrow A in FIG. 2.

DESCRIPTION OF THE PREFERRED EMBODIMENTS.

With reference to the figures of the drawings, 1 denotes in its entirety an aspirator, constituted by a pump 1a and an electric motor 1b, from an aspiration conduit 2 originates and connects the aspirator to a closed environment 13. The aspirator extracts air from the closed environment 13 through the conduit 2 as shown by arrow A in FIG. 1. A discharge conduit 2a is connected to the aspirator 15 for removing the air aspirated therefrom as shown by arrow B in FIG. 1.

Leading out of the aspiration conduit 2 there is a cylindrical sleeve 5, a first end 5a of which is connected to the aspiration conduit 2 and a second end of which 5b is connected to the outside environment. An annular seating 9 is afforded in the sleeve 5, to which an obturator 7, predisposed inside the sleeve 5, is associated.

The obturator is normally in a closed position, i.e. pressed against the seating 9, in which position the obturator 7 prevents passage of air through the sleeve 5.

The obturator 7 is kept pressed against the seating 9 by an elastic element, in the illustrated embodiment a helix spring 8, which is preloaded at a predetermined load, and is loaded against the opening of the obturator 7. A chamber is afforded inside the obturator 7, which chamber 10 is filled with a material having a high heat-dilation coefficient, for example a thermometric liquid. An end of a rod 11 projects from the chamber 10, which rod 11 is slidable in an axial direction and another end of which is inserted in the chamber 10, sunk in the thermometric liquid. The section of the exit hole of the rod 11 from the chamber 10 is completely occupied by the section of the rod 11 itself, in order to prevent any exiting of material from the chamber 10. A striker element 12, fixed with respect to the sleeve 5, is constrained to the end of the rod 11 projecting from the chamber 10. This striker element 12, which in the figures is illustrated as a metal bar arranged diametrically and constrained to the ends of the external surface of the sleeve 5, is arranged in such a way that it obstructs an externalwise sliding by the rod 11. For this purpose the striker element 12 is arranged above the end of the rod 11 which exits from the chamber 10.

The above-described device realises a first valve 4 and a second valve 6 which have a common seating and obturator, and therefore which both act in opening or closing the connection between the aspiration conduit 2 and the outside environment. The two valves are, however, differently controlled and are independent from each other, and are functionally different and distinct. The opening and closing of the first valve 4 is commanded by the temperature in the outside environment. When the outside temperature increases, the material contained in the chamber 10 dilates and pushes the rod 11 externalwise; the rod 11 then pushes against the striker element 12 and thus pushes the obturator 7 away from the seating 9, opening the valve 4 and placing the aspiration conduit 2 in communication with the outside environment. The quantity of thermometric material, the section of the rod 11 and its initial distance from the striker element 12 are calculated in such a way as to cause an opening of the valve when the external temperature rises above a predetermined level, normally comprised between 45° C. and 55° C.

The opening and closing of the second valve 6 is commanded by the difference between the closed environment 3 and the outside environment. When this difference, to which a precise absorption of electric current corresponds, and therefore a precise coil temperature, overcomes the load on the spring 8, the obturator 7 distances from the seating 9 and opens the valve, setting the aspiration conduit 2 in communication with the outside environment. This functioning of the valve 6, activated by a motor coil temperature of between 90° C. and 120° C., is similar to the functioning of known valves mounted on aspirators of known type.

When, in any one of the above-described ways, the connection between the aspiration conduit 2 and the outside environment is opened, the absorption of electric current by the aspirator motor is drastically reduced, as is the performance of the motor (which the user will notice in the guise of a fault), and the production of heat by the motor. The reduction of heat by the machine and/or an intervention by the user, i.e. making more cool air available to the machine in order to reduce the outside temperature in the surrounding atmosphere, cause the valves to close and bring the machine back into conditions of normal operation, without having to shut the machine down. The above-described device behaves as a normal, known-type overpressure valve for the current absorbed by the motor when the temperature is within normal parameters, while it becomes an added protection cutoff when the temperature limits are exceeded.

If the device is applied not on an aspirator but on a compressor, the 15 conformation of the device will be slightly different as air delivered to closed environment 13 will move in a direction opposite to that of arrows A and B as shown by arrows C and D. The device will be located on the delivery conduit, the obturator will open externalwise and the rod will move in an opposite direction against an internal striker element; but its functioning will be altogether similar to what is described above.

What is claimed:

1. A device for regulating an aspirator, comprising, an aspiration conduit which conduit connects the aspirator to a closed environment, through which conduit air is extracted from the closed environment;

wherein the device also comprises a first valve arranged between the conduit and an outside environment; wherein the first valve is normally closed when a temperature of the outside environment is below a predetermined temperature and open when a temperature of the outside environment is above a predetermined temperature, placing the conduit in communication with the outside environment;

a second valve of known type which is located between the conduit and the outside environment, an opening and closing of which second valve is controlled by a predetermined pressure differential between the closed environment and the outside environment, wherein the first valve and the second valve have an obturator in common, wherein an opening and closing movement of which are controlled independently both by a reaching of the predetermined pressure differential between the closed environment and the outside environment and by a reaching of the predetermined temperature of the outside environment, and wherein the first valve and the second valve are made in a sleeve, a first end of which is connected to the conduit and a second end of which is connected to the outside environment, and in which sleeve a seating is made for the first valve and the second valve, and which sleeve houses the obturator; an opening of the obturator being opposed by an elastic element; a chamber being afforded internally of the obturator, which chamber is filled with a material having a high coefficient of heat dilation and from an end of which chamber an end of a rod projects, which rod is slidable in an axial direction, and another end of which rod is inserted in the chamber; there being also a striker element, fixed with respect to the sleeve, which striker element is conformed and arranged in such a way as to oppose an external-wise sliding of the rod.

2. A device for regulating a compressor, comprising, a delivery conduit, which conduit connects the compressor to a closed environment, through which conduit air is introduced, to the closed environment;

wherein the device also comprises a first valve arranged between the conduit and an outside environment, wherein the first valve is normally closed when a temperature of the outside environment is below a predetermined temperature and open when a temperature of the outside environment is above a predetermined temperature, placing the conduit in communication with the outside environment a second valve of known type which is located between the conduit and the outside environment, wherein an opening and closing of the second valve is controlled by a predetermined pressure differential between the closed environment and the outside environment, wherein the first valve and the second valve have an obturator in common, an opening and closing movement of the obturator are controlled independently both by a reaching of the predetermined pressure differential between the closed environment and the outside environment and by a reaching of the predetermined temperature of the outside environment, wherein the first valve and the second valve are made in a sleeve, a first end of which is connected to the conduit and a second end of which is connected to the outside environment, and in which sleeve a seating is made for the first valve and the second valve, and which sleeve houses the obturator; an opening of the obturator being opposed by an elastic element; a chamber being afforded internally of the obturator, which chamber is filled with a material having a high coefficient of heat dilation and from an end of which chamber an end of a rod projects, which rod is slidable in an axial direction, and another end of which rod is inserted in the chamber; there being also a striker element, fixed with respect to the sleeve, which striker element is conformed and arranged in such a way as to oppose an external-wise sliding of the rod.

* * * * *